United States Patent [19]

Sandel et al.

[11] Patent Number: 4,842,138
[45] Date of Patent: Jun. 27, 1989

[54] RIGID DISPOSABLE CONTAINER FOR HOLDING AND DISPENSING OF USED MEDICAL SHARPS AND OTHER MEDICAL-SURGICAL MATERIALS

[75] Inventors: Dan Sandel, Tarzana; Mike Hoftman, Northridge, both of Calif.

[73] Assignee: Devon Industries, Inc., Chatsworth, Calif.

[21] Appl. No.: 169,172

[22] Filed: Mar. 10, 1988

Related U.S. Application Data

[63] Continuation of Ser. No. 838,296, Mar. 10, 1986.

[51] Int. Cl.⁴ .............................................. B65D 83/10
[52] U.S. Cl. .................... 206/370; 206/363; 206/366; 206/438; 220/1 T; 220/345; 220/346
[58] Field of Search ...................... 206/45.34, 363, 364, 206/366, 370, 438, 439, 571, 602, 621, 519; 220/1 T, 306, 345, 346

[56] References Cited

U.S. PATENT DOCUMENTS

| 2,667,422 | 1/1954 | Kauffman | 206/519 |
|---|---|---|---|
| 3,362,564 | 1/1968 | Mueller | 220/346 |
| 3,791,514 | 2/1974 | Watanabe | 220/346 |
| 3,811,565 | 5/1974 | Tancredi | 206/45.34 |
| 4,013,109 | 3/1977 | Sandel | 150/52 R |
| 4,304,330 | 12/1981 | Winkler | 206/45.34 |
| 4,341,091 | 7/1982 | Minter | 206/519 |
| 4,375,849 | 3/1983 | Hanifl | 206/366 |
| 4,418,821 | 12/1983 | Sandel | 206/370 |
| 4,421,245 | 12/1983 | Schultz et al. | |
| 4,421,246 | 12/1983 | Schultz et al. | 220/306 |
| 4,445,611 | 5/1984 | Shofu | 206/45.34 |
| 4,452,358 | 6/1984 | Simpson | 206/366 |
| 4,454,944 | 6/1984 | Shillington et al. | 206/366 |
| 4,466,538 | 8/1984 | Gianni | 206/370 |
| 4,488,643 | 12/1984 | Pepper | 206/370 |
| 4,494,652 | 1/1985 | Nelson et al. | 206/370 |
| 4,520,926 | 6/1985 | Nelson | 206/370 |
| 4,552,280 | 11/1985 | Owen et al. | 206/370 |
| 4,580,688 | 4/1986 | Harris et al. | 220/1 T |
| 4,667,821 | 5/1987 | Shillington | 206/366 |

FOREIGN PATENT DOCUMENTS 2740335 3/1979 Fed. Rep. of Germany ...... 206/366

Primary Examiner—David T. Fidei
Attorney, Agent, or Firm—Poms, Smith, Lande & Rose

[57] ABSTRACT

A rigid, disposable container for safety containing and disposing of medical-surgical materials, including needles, syringes, scalpels and dressings after use, comprises five, lightweight plastic pieces which snap together without tools to form a closed container having a one-way barrier at a larger opening for the insertion of used materials therethrough, which barrier can be removed if desired, and additional apertures having sharps-removing features molded therein to permit the simultaneous removal of sharps from associated devices and their disposal therethrough. A flush, lockable, sliding cover is provided on the container to close the disposal openings against passage of macroscopic material either partially during use or completely before disposal.

17 Claims, 6 Drawing Sheets

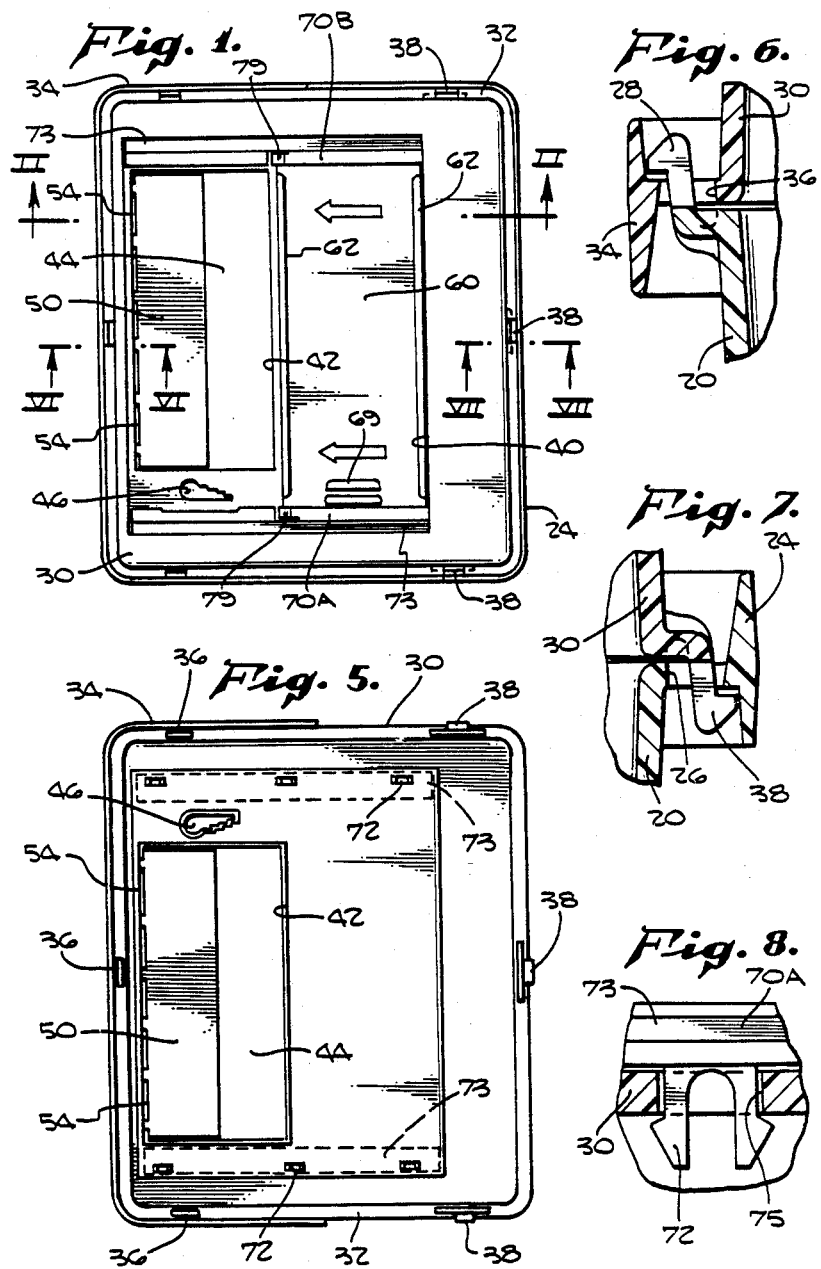

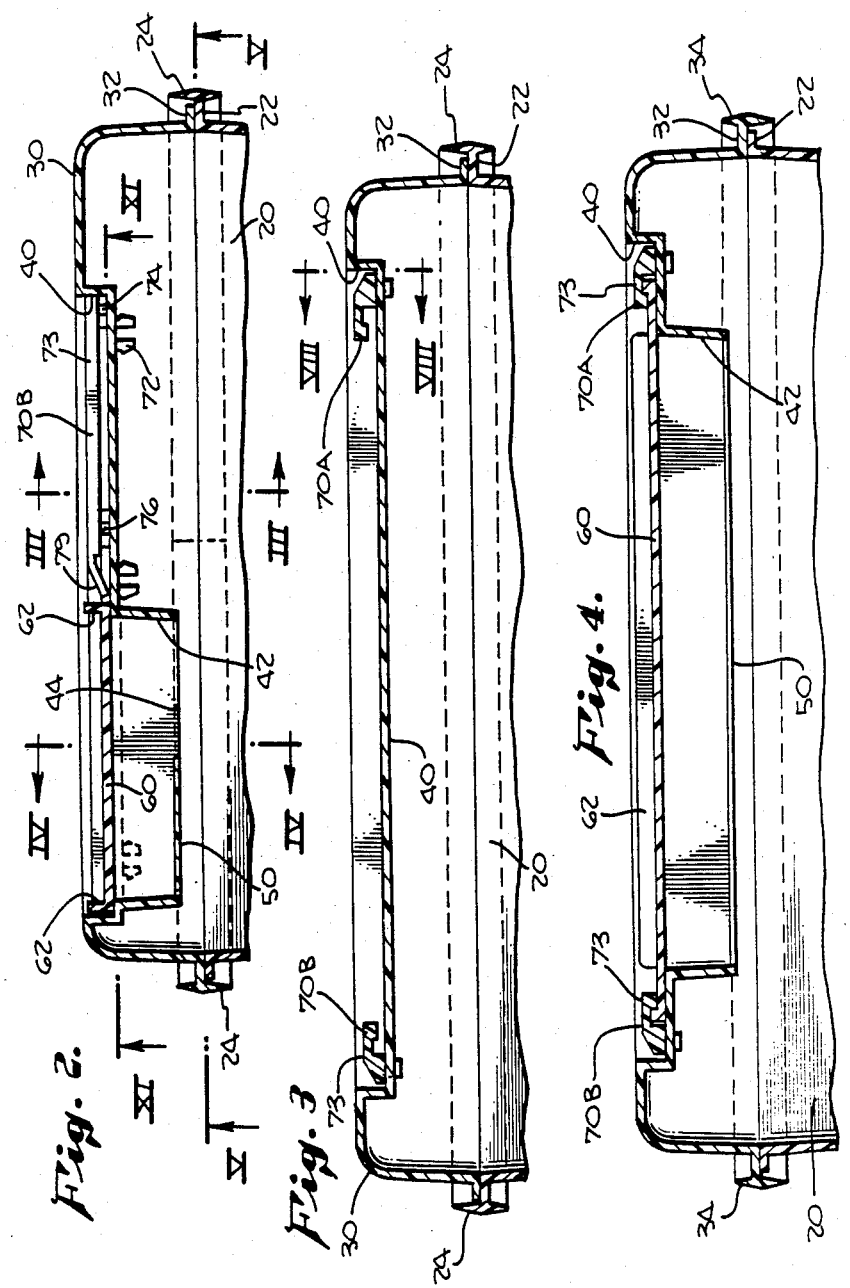

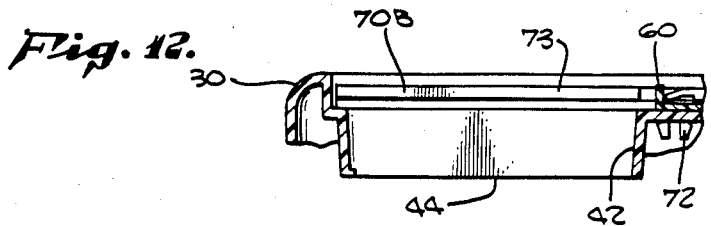
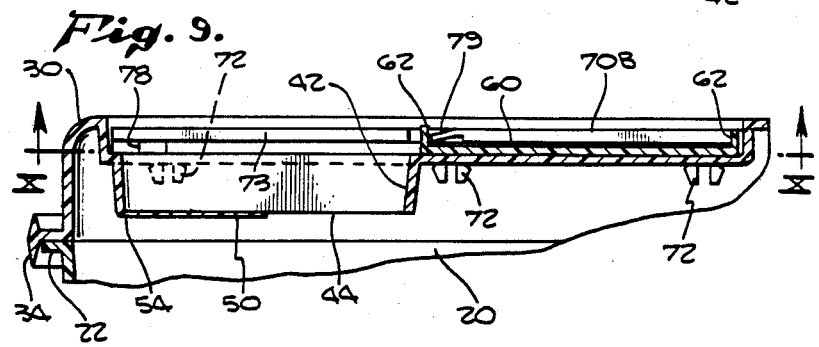
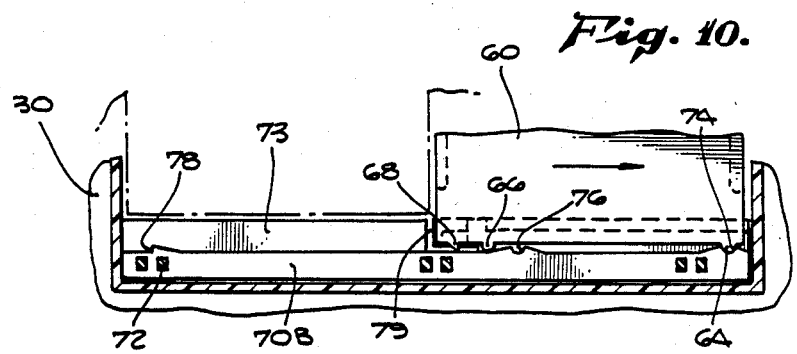
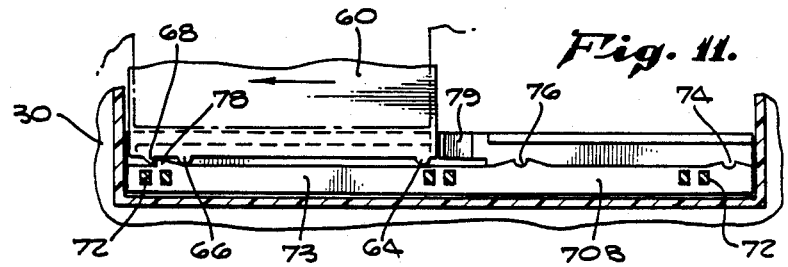

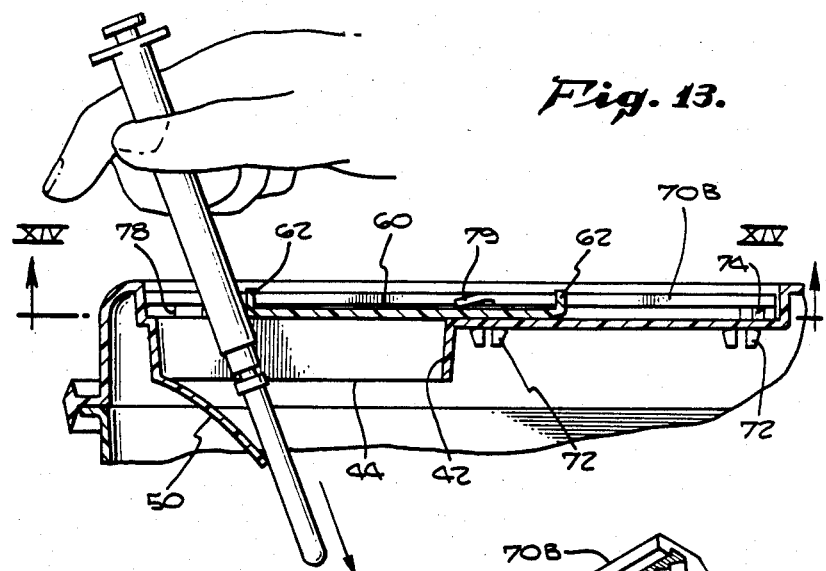
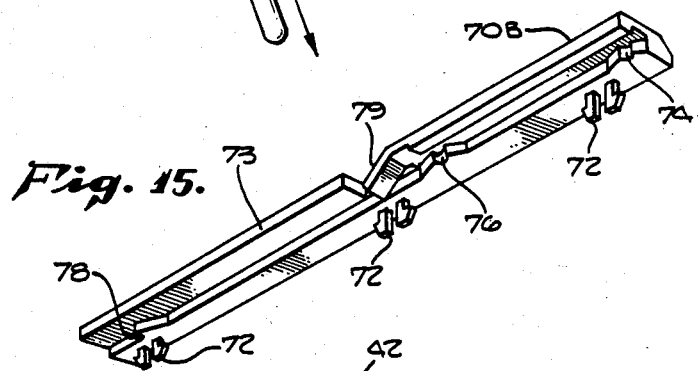
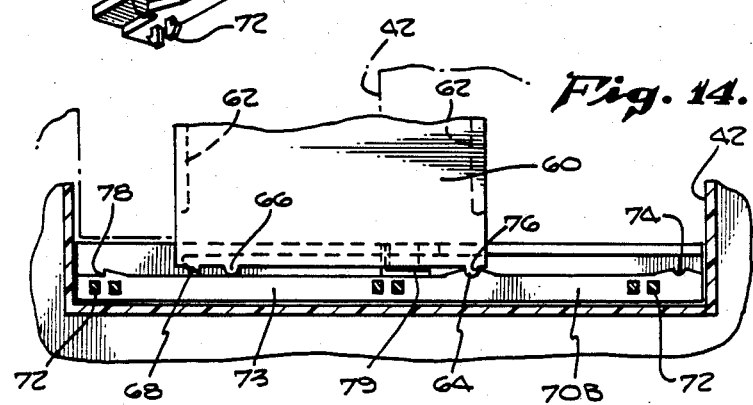

RIGID DISPOSABLE CONTAINER FOR HOLDING AND DISPENSING OF USED MEDICAL SHARPS AND OTHER MEDICAL-SURGICAL MATERIALS

This is a continuation of co-pending application Ser. No. 838,296 filed on March 10, 1986.

BACKGROUND OF THE INVENTION

1. Field of The Invention

This invention relates, in general, to medical-surgical supplies for hospitals, and more particularly, to rigid, disposable containers for used medical-surgical materials, including "sharps", e.g., hypodermic needles, suture needles and scalpel blades.

2. Summary of The Prior Art

This decade has seen an acceleration of the trend in the medical-care-provision field of disposable, one-use medical-surgical devices and materials. This trend is away from the former procedure of sterilization and re-use of these devices, both to reduce the high labor costs involved in the sterilization and to insure that materials and devices used are completely sterile. Cost tradeoffs have shown this use-and-dispose philosophy compares quite favorably with the previous method.

Present hospital protocol in those institutions employing the use-and-dispose philosophy entails the assembly and distribution by unskilled personnel of a clean, but not sterilized, flexible plastic or paper container to those locations where containment is required, viz., operating rooms, nurses' stations, soiled linen rooms, and emergency rooms or so-called "med/surg" rooms, i.e., those where simple, out-patient surgery is performed.

Thus, it is not intended that these containers be used in the "sterile field" of the operating room, for example, but rather on the "back table" of the operating room, well outside of the sterile field, where the "sterile nurse" passes the used materials to be disposed of to the "circulating nurse", who then disposes of the materials in the container.

After the containers are filled, they are typically collected by unskilled housekeeping personnel and taken for disposal. In some states, this involves processing of the used materials by incineration, and in some states, by law, the materials are "red-bagged" or boxed, and stored for pick-up by contract disposal personnel. They, in turn, transport the materials to be disposed to another location where they are autoclaved under low-pressure steam for a predetermined time to sterilize them, then rebagged and taken to a landfill for burial.

Experience has taught that this disposal chain affords ample opportunity for unskilled personnel to be injured and/or contaminated by contact with used medical-surgical materials.

Thus, a problem created by the use-and-dispose philosophy is that of containing and disposing of the used materials, much of which includes dangerously-sharp implements referred to as "sharps" in the field, both within the hospital environment and in the disposal chain.

Another, and related problem is the safe containment until disposal of those sharps which might be put to illicit uses, e.g., hypodermic needles, were they to fall into unauthorized hands.

Yet another problem created by the disposal of medical-surgical materials is the containment of the potentially-contaminated, used materials in a controlled volume to prevent the contamination of the surrounding, sterile surfaces and materials until the contaminated materials can be disposed of.

Still yet another problem associated with the disposal philosophy is that of the need for the sterilization of the container for the used medical-surgical materials itself, which must be sterilized after use before bringing it back into contact with a relatively-clean environment.

Thus, it would be desirable to have an inexpensive, rigid, tamper-resistant container for safely holding and disposing of the used medical-surgical material, which is itself entirely disposable, in keeping with the use-and-dispose philosophy.

SUMMARY OF THE INVENTION

It is therefore an object of the present invention to provide an inexpensive, simple, rigid but lightweight container for the storage and disposal of used medical-surgical materials.

It is yet another object of the present invention to provide such a container to hold and dispose of medical sharps safely, and to prevent casual access to controlled implements, particularly hypodermic needles and syringes, by unauthorized persons.

It is still yet another object of the present invention to provide a holding container for used medical-surgical materials in a manner which prevents their contamination of the surrounding, sterile area.

It is still yet another object of the present invention to provide a container which may be disposed of simultaneously with the disposal of the used medical-surgical materials, thereby obviating the need to sterilize the container itself.

These objects, and other advantages, are preferably accomplished in a container made of inexpensive, lightweight but rigid, disposable, injection-molded plastic, comprising a top and bottom which can be easily assembled together by unskilled personnel without the use of tools to form the enclosure, the top having a plurality of apertures through which used medical-surgical materials may be inserted one-way into the container, including a larger aperture guarded by a one-way barrier which snaps shut after the insertion of larger used materials. The barrier is selectively removable by the user to provide a more "open" container, and a flush-mounting cover is provided on the container, the position of which is adjustable by the user, to close the openings of the container either partially during use or completely before disposal.

DESCRIPTION OF THE DRAWINGS

A more complete understanding of the invention may be obtained by a review of the following description of the preferred embodiment, when taken in conjunction with the drawings, wherein:

FIG. 1 is a view of the top of the enclosure with the sliding cover slid back from the disposal openings of the container, and wherein sections II—II, VI—VI and VII—VII are taken;

FIG. 2 is a sectional view through the container as revealed by taking section II—II in FIG. 1, and showing a view through the top part, with the sliding cover in the closed position;

FIG. 3 is another sectional view through the top part as revealed by section III—III taken in FIG. 2;

FIG. 4 is yet another sectional view through the top part, as revealed by taking the section IV—IV in FIG. 2;

FIG. 5 is a view looking into the bottom of the top part of the container as revealed by taking the section V—V in FIG. 2;

FIG. 6 is a sectional view through the molded, male-female snap-fitting which holds the top of the container to the bottom in the assembled position, as revealed by taking section VI—VI in FIG. 1;

FIG. 7 is another sectional view through the top-to-bottom fastener mechanism, as revealed by the section VII—VII taken in FIG. 1;

FIG. 8 is a detailed section through the cover slide rail and the container top revealed by the section VIII—VIII taken in FIG. 3, showing the snap-in, over-center type fastener used to install the rail to the container top;

FIG. 9 is a partial sectional view through the top part of the container with the sliding cover shown in the fully-opened position;

FIG. 10 is a sectional view through the underside of the top part of the container with the cover shown in the fully-opened position, as revealed by the section X—X taken in FIG. 9;

FIG. 11 is the same as FIG. 10, except that the sliding cover is shown in the fully-closed, locked position;

FIG. 12 is a partial sectional view through the disposal opening of the top part of the container showing the barrier flap removed;

FIG. 13 is a partial sectional view through the side of the top part of the container showing the cover in the intermediate position and the disposal of a hypodermic syringe and needle combination into the container in the direction of the arrow, with the barrier flap in a partially-displaced position;

FIG. 14 is a partial sectional view into the underside of the top part of the container showing the sliding cover in the intermediate position, as revealed by the section XIV—XIV taken in FIG. 13;

FIG. 15 is an isometric view of the underside of one of the two slide rails;

DESCRIPTION OF THE PREFERRED EMBODIMENT

Figure 16:
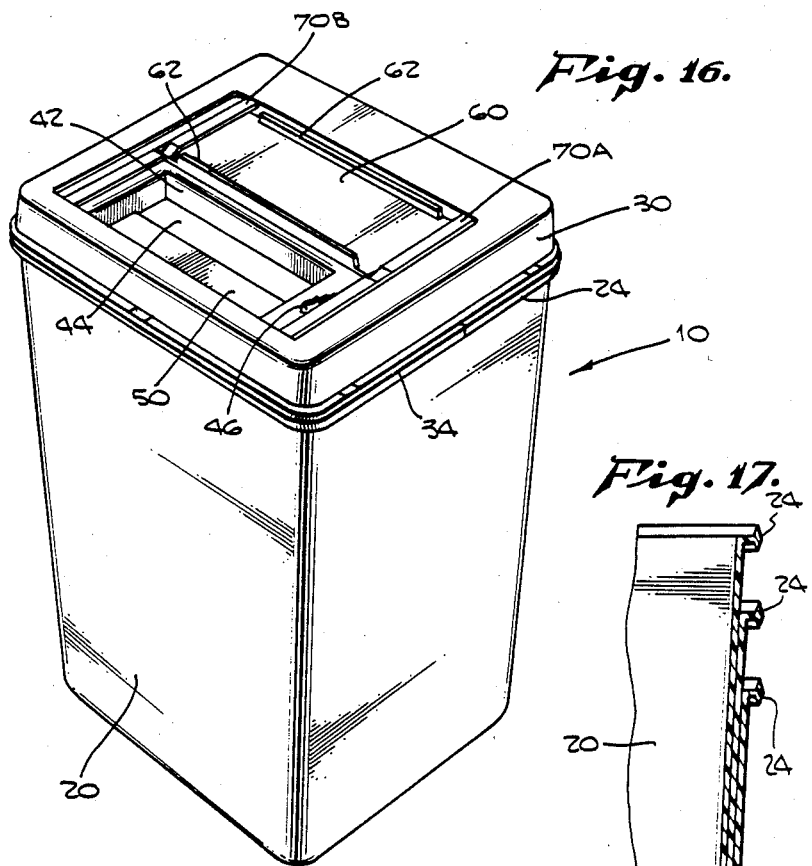
FIG. 16 is an isometric view of the assembled container with the sliding cover shown in the fully-open position.
Figure 19:
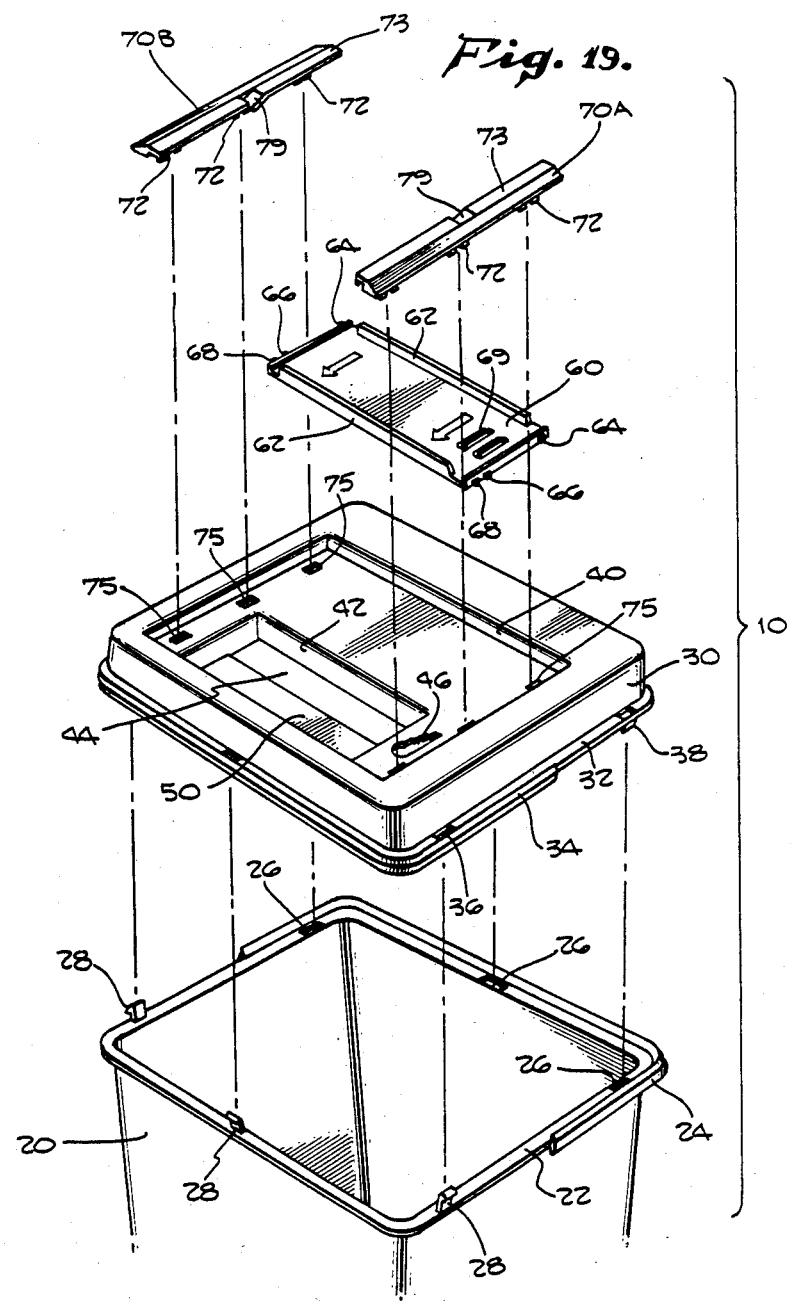
FIG. 19 is a partial, isometric, exploded view of the container of the present invention showing the parts of the bottom, the top, the sliding cover and the cover retaining rails.

FIGS. 16 and 19 best illustrate a preferred embodiment of the subject of the present invention, a disposable container for medical sharps and other medical-surgical materials 10, FIG. 16 being an isometric view of the assembled container 10 and FIG. 19 being an exploded view, showing the parts in their relative relationship to one another.

Container 10 comprises five snap-together parts: A bottom part 20, a top part 30, a sliding cover 60 and two cover-retaining rails 70A and 70B which are symmetrically-similar to one another.

It is contemplated that, in the preferred embodiment of the container 10, all parts are injection-molded from a strong but lightweight and inexpensive thermoplastic such as polyethylene or polypropylene. This results in a container that is relatively strong, rigid, decoratively colorful, but sufficiently inexpensive to warrant a one-use disposal.

Additionally, if top part 30, cover 60 and slide rails 70A and 70B are molded from a transparent or transculent material, the contents of the container may be easily viewed, and the remaining disposal volume available easily estimated.

These modes and materials of fabrication also permit the inclusion of details within the molds to incorporate within the parts certain advantageous features discussed below, e.g., the "nesting" ability of the parts and the snap-together fasteners of the container 10. The thermoplastic material of the parts further permits the inclusion of a very smooth, finished surface on both the inside and the outside of the container, which helps to prevent the entrapment of potentially septic material on the internal or external surface of the container 10.

Bottom part 20 consists essentially of an enclosure with an open top having a flange 22 at the periphery thereof for mating with a similar flange 32 on top part 30. A guide lip 24 encircles one half of the periphery of flange 22 and aids in lending strength and rigidity to the mating flange 22, while serving as a guide for assembly with top part 30.

Because of the mode and materials of fabrication selected for container 10, these fastening details are easily added to the mold to permit their inclusion as part of the molded product and permit the parts of the container 10 to snap together without the use of tools of any kind. Disposed about mating flange 22 are a plurality of snap-together fastening means 26 and 28. The detail of these fasteners is best illustrated in FIGS. 6 and 7, and include a female opening 26 in mating flange 22 to receive mating, over-center male members 38 located on the top part 30, as well as upward-facing, over-center male members 28 on bottom part 20 which are received in corresponding female openings 36 on top part 30. However, when the parts are once snapped together, they are not easily disassembled without some effort and the use of tools, which renders the contents of the container relatively tamper-resistant.

Top part 30 consists of an enclosure with an open bottom having a mating flange 32 encircling its entire periphery. A guide lip 34 similar to the guide lip 24 on the bottom 20, is molded onto half of the top's mating flange 34 such that, when the top 30 is installed onto bottom 20, guide lips 24 and 34 encircle the parting line between top 30 and bottom 20 and serve to reinforce the mating flanges of the two parts, as well as guide members to guide the two parts together during assembly.

Mating flange 32 has, like that of the bottom part mating flange 22 immediately below it, a plurality of snap-together fastener means molded into it during fabrication. Again, reference is made to FIGS. 6 and 7, wherein male, over-center tabs 38 located on top part 30 engage with female fastener openings 26 located on bottom part 20, and female openings 36 on top part 30 receive male, over-center tabs 28 located on bottom part 20.

Molded into the upper surface of top part 30 are a pair of recesses, 40 and 42. The lower of these recesses includes a large opening 44 through which larger medical-surgical materials may be inserted into container 10, as well as a smaller opening 46 having specialized, tool-gripping surfaces molded in its periphery to permit its engagement of, and the disengagement of, certain medical sharps from their associated devices. In the embodiment illustrated, opening 46 comprises an aperture for Luer-type hypodermic needles of various sizes. By inserting a hypodermic needle mounted onto a hypodermic syringe into opening 46, the user may, by simply twisting the syringe in a clockwise or anti-clockwise direction, cause the needle to be disengaged from the syringe, whereby it will fall into the disposal volume of container 10. This enables the disposal of the used hypodermic needle, while permitting the syringe to be retained for sterilization and further use by those institutions which have not switched to completely-disposable hypodermic syringes. The entire used syringe and needle may be disposed of through larger opening 44, as illustrated in FIG. 13.

The large opening 44 on container 10 is provided with a rectangular barrier flap 50, molded into top part 30 at the level of the large opening 44, which is attached at one edge to permit the flap to swing inwardly into the container when used medical-surgical materials are inserted therethrough. Barrier flap 50 covers all or a portion of large opening 44 and guards the internal volume of container 10 against the egress of discarded materials and renders the large opening 44 of container 10 relatively tamper-resistant. However, if desired, barrier flap 50 may be removed by the user to provide an unimpeded large opening 44 into container 10, a feature which may be desirable from the standpoint of some practitioners. To accomplish this, barrier flap 50 is provided with a series of serrations 54 at the hinged edge where it joins with top part 30. By repeated flexing of barrier flap 50 back and forth within large opening 44, the flap can be broken off to provide an unimpeded opening 44.

The upper recess 40 of top part 30 provides a mounting surface for a flush, sliding cover 60. Sliding cover 60 is provided with a pair of right-angled, vertical extensions 62 at the front and rear edges, respectively, which function as handles and cover stops against the front and rear sidewalls of upper recess 40 in the cover-closed and open positions, respectively.

Sliding cover 60 additionally is provided with a pair of rounded nose pieces 64 at its rear edge, a second pair of rounded nose pieces 66 intermediate between the cover's front and rear edges, and a pair of locking nose pieces 68 at its front edge, all of which lie in the plane of cover 60 and extend outwardly from the side edges. The purpose of these nose pieces is best illustrated in FIGS. 10, 11, and 14, showing the operation of cover 60 in the fully-open, fully-closed and intermediate positions, respectively.

Cover 60 is retained in upper recess 40 by a pair of symmetrical cover rails 70A and 70B, which snap-fit into apertures 73 located in top part 30. Apertures 73 receive over-center, snap-fit prongs of fastener 72 molded into slide rails 70A and 70B, to permit the rails to be snapped into place without tools either before or after the cover is positioned in upper recess 40. This fastening feature for rails 70A and 70B is best illustrated in FIG. 8.

Cover-retaining rails 70A and 70B may be seen illustrated in cross section in FIGS. 3 and 4, and isometrically in FIG. 15. Each rail includes a retaining flange 73 which are offset above the floor of upper recess 40, and serve to overlap and retain the edges of sliding cover 60 therebetween. On the lower, inside, facing edges of rails 70A and 70B are a pair of rounded detents 64, located on the rear end of the rails, an intermediate pair of rounded detents 76, and a pair of locking detents 78, located at the front ends of the rails. This arrangement permits sliding cover 60 to be retained in a fully-open position (FIG. 10) or a partially-closed position (FIG. 9) by the engagement of the rear pair of rounded nose pieces 64 in the pair of rearmost rounded detents 74 or the intermediate pair of rounded detents 76, respectively. The intermediate pair of rounded detents 76 are located on rails 70A and 70B such that the front edge of sliding cover 60 is retained at a position which overlaps the inner edge of barrier flap 50, such that disposal opening 44 is narrowed to a width which prevents the entry of the fingers into the interior of the container while permitting the disposal of narrower medical-surgical materials, such as hypodermic syringes or used scalpels.

In the fully-closed position (FIG. 11), sliding cover 60 is "locked" into position by a pair of special detents 78 in rails 70A and 70B, which detents 78 contain an over-center feature to firmly engage locking nose parts 68 at the front edge of cover 60 to prevent the cover from being easily reopened. It is intended by this arrangement to provide a means to render the container 10 more tamper-resistant and leak-proof after the container 10 has been filled and is ready for disposal.

Each retaining flange 73 of cover-retaining rails 70A and 70B contains a notched, down-turned portion 79, which permits the rails to be installed on top part 30 before sliding cover 60 is installed. Sliding cover 60 may then be installed between the sliding rails 70A and 70B and below retaining flanges 73 by drawing the front edge of sliding cover 60 down the upper surface of down-turned flanges 79 and drawing the cover forward until the rear edge of cover 60 is past the down-turned flanges 79.

Sliding cover 60 is provided with a vent opening 69 such that, when sliding cover 60 is in the fully-closed, locked position, the contents of container 10 may be autoclaved with steam for sterilization of the contents prior to disposal, as required by law in some states.

Figure 17:
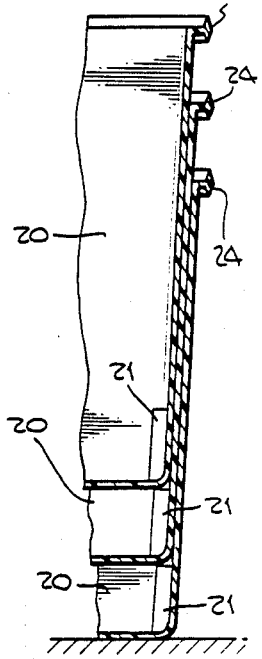
FIG. 17 is a partial sectional view which illustrates that a number of bottom parts of the container may be nested within one another for efficient packing.
Figure 18:
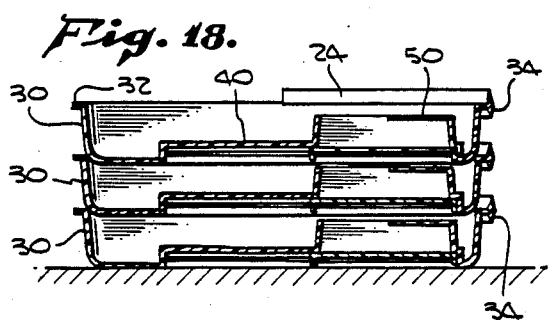
FIG. 18 is a sectional view through a number of top parts of the container, illustrating the nesting feature of this part.

Another product of the molding process and plastic materials selected for container 10 is the presence of draft angles incorporated into the parts as a consequence of the necessity for the removal of the parts from the mold. This draft angle may be utilized advantageously to permit both the bottom parts 20 and the cover parts 30 to be "nested" or stacked within one another for handling and shipment, for convenience, and to conserve shipping volume. This nesting of parts for shipment is best illustrated in FIGS. 17 and 18, and it is intended that the bottom part 20 incorporate a spacer boss 21 appropriately disposed on the internal surface of the part to provide a small amount of space between the parts when stacked to prevent their sticking together during shipping and handling.

Those skilled in the art will recognize that the foregoing materials, methods of fabrication and detail features are suggested for illustration purposes only, and can be suitably modified to provide a variety of disposable container shapes, styles and functions.

Accordingly, our invention, a rigid container for holding and disposing of used medical-surgical materials and sharps, should be limited in its scope only by the appended claims.

We claim:

1. A rigid container for holding and disposing of used surgical sharps and other medical-surgical materials, comprising:

enclosure means for rigidly enclosing a space to contain said disposed medical-surgical materials, wherein said enclosure means further comprises a first part having an open top and faster means disposed thereon; and a second part having an open bottom and fastener means disposed thereon to engagably-mate and fasten with said first part to form said rigidly enclosed space, said enclosure means having at least one aperture therethrough to permit the passage of said materials into said space; and one-way barrier means at said at least one aperture to permit the insertion of said medical-surgical materials therethrough into said space and to prevent the passage of said materials therefrom, said barrier means comprising rigid flap means disposed substantially across a portion only of said aperture to form a barrier hingably-attached at one edge to said enclosure means and so disposed to hinge inwardly to said space when displaced by said insertion of said medical-surgical materials therethrough and to return to said normally-closed position otherwise; wherein:

said aperture for the passage of said medical-surgical materials therethrough has an area slightly larger than the area of a transverse plane through an average human hand; and said flap means further includes a leaf molded into said enclosure at said aperture along one edge of said leaf to extend substantially entirely across said aperture in a direction parallel to said edge and only partially across said aperture in a direction perpendicular to said edge such that said leaf blocks a portion only of said aperture; and such that said leaf blocks a portion only of said aperture; and closure means are provided in addition to said barrier means attached to said enclosure means to close at least one aperture against the further insertion or removal of said medical-surgical materials therethrough.

2. A rigid container for holding and disposing of used surgical sharps and other medical-surgical materials, comprising:

enclosure means for rigidly enclosing a space to contain said medical-surgical materials, wherein said enclosure means further comprises a first part having an open top and faster means disposed thereon; and a second part having an open bottom and fastener means disposed thereon to engagably-mate and fasten with said first part to form said rigidly enclosed space, said enclosure means having at least one aperture therethrough to permit the passage of said materials into said space; and one-way barrier means at said at least one aperture to permit the insertion of said medical-surgical materials therethrough into said space and to prevent the passage of said materials therefrom, said barrier means comprising rigid flap means disposed substantially across a portion only of said aperture to form a barrier hingably-attached at one edge to said enclosure means and so disposed to hinge inwardly to said space when displaced by said insertion of said medical-surgical materials therethrough and to return to a normally-closed position otherwise; wherein:

said aperture for the passage of said medical-surgical materials therethrough has an area slightly larger than the area of a transverse plane through an average human hand; and said flap means further includes a leaf molded into said enclosure at said aperture along one edge of said leaf such that said leaf blocks a portion only of said aperture;

closure means are provided in addition to said barrier means attached to said enclosure means to close said aperture against the further insertion or removal of said medical-surgical materials therethrough; and means are located along said edge of said leaf to enhance the flexibility of said hinge and including a plurality of fenestrations to permit said leaf of said barrier means to the selectively removed.

3. The container of claim 1, wherein said closure means further comprises:

a cover movably attached to said enclosure means, having the same or slightly larger area than said at least one aperture, said cover selectively movable to one of a plurality of positions with respect to said aperture to close all, some or none of said at least one aperture; and means for movably-attaching said cover to said enclosure and for retaining said cover in said one selected position with respect to said at least one aperture.

4. A rigid container for holding and disposing of used medical sharps and other medical-surgical materials comprising:

a molded, plastic bottom part having an open top with a flange molded thereon, said bottom part flange having fastener means molded therein;

a plastic top part having an open bottom with a flange for mating with said bottom part flange molded thereon, said top part flange having a plurality of fastener means molded therein to engage said bottom part flange fastener means and fasten said top part to said bottom part without tools to form said container, said top part further having a pair of stepped recesses in an upper surface, said top part further having at least one aperture therethrough in the lower of said stepped recesses to permit the insertion therethrough of medical-surgical materials, said at least one aperture being substantially the size of a hand, said top part further having a one-way barrier across said at least one aperture, comprising a closure flap molded into said top part along one edge of said flap to hinge said flap for inward deflection with respect to said top part upon insertion of said medical-surgical materials therethrough, said closure flap covering all, or a portion of, said aperture, said top part further having a plurality of fenestrations along said edge hinging said closure flap to said top part to permit said flap to be selectively broken away to remove said barrier;

a flat, plastic cover having a pair of raised handle-stops at the front and back edges and a plurality of nose parts along the side edges, said cover being slidably mounted to said top part flush within the upper of said pair of recesses in said top part and above said at least one aperture to permit said cover to be moved selectively over said at least one aperture to close all, some or none of said at least one aperture; and a pair of sliding rails having fasteners to fasten said rails to said top part within the upper of said recesses of said top part, and a retaining flange to slidably retain said cover in position between said rails and said top part in said upper recess, said rails each having a plurality of detents to mate and engage with said nose parts of said cover to permit the position of said cover to be adjusted with respect to said aperture, said retaining flanges each having a notched, down-turned portion intermediate of the length thereof to permit said cover to be installed below said flanges after said rails are installed on said top part;

said top part having a plurality of fastener openings to receive said rail fasteners to hold said rails in place.

5. The container of claim 4 further comprising:

at least one additional aperture through said container having a sharps-engaging surface molded into its periphery to grasp said sharps for disengagement of said sharps from an associationed medical-surgical device, whereby the sharps may fall through said at least one additional aperture into said container.

6. The container of claim 5, wherein:

said additional aperture is configured to engage a plurality of "Luer"-type hypodermic needle sizes.

7. The container of claim 5, wherein:

said at least one additional aperture is configured to engage a plurality of "Vacutainer"-type hypodermic needle sizes.

8. The container of claim 4, wherein:

said bottom part and said top part are provided with boss means molded therein to permit stacking of a plurality of said bottom and top parts within each other without sticking.

9. The container of claim 4, wherein:

said top part is fabricated from a transparent or translucent material such that the contents of said container may be visualized.

10. A rigid container for holding and disposing of used medical sharps and other medical-surgical materials comprising:

a molded, plastic bottom part having an open top with a flange molded thereon;

a plastic top part having an open bottom with a flange for mating with said bottom part flange molded thereon, said top part flange having a plurality of fastener means molded therein to engage said bottom part flange and fasten said top part to said bottom part without tools to form said container, said top part further having at least one aperture therethrough to permit the insertion therethrough of medical-surgical materials, said at least one aperture being substantially the size of a hand, said top part further having a one-way barrier in said at least one aperture and comprising a single closure flap molded into said top part along one edge of said flap to hinge said flap for inward deflection with respect to said top part upon insertion of said medical-surgical materials therethrough, and outwardly otherwise, said closure flap extending substantially entirely across said aperture in a direction parallel to said one edge and only partially across said aperture in a direction perpendicular to said one edge, a flat, plastic cover slidably mounted to said top part and above said at least one aperture to permit said cover to be moved selectively over said at least one aperture to close all, some or none of said at least one aperture.

11. A rigid container for holding and disposing of used medical sharps and other medical-surgical materials comprising:

a molded, plastic bottom part having an open top with a flange molded thereon;

a plastic top part having an open bottom with a flange for mating with said bottom part flange molded thereon, said top part flange having a plurality of fastener means molded therein to engage said bottom part flange and fasten said top part to said bottom part without tools to form said container, said top part further having at least one aperture therethrough to permit the insertion therethrough of medical-surgical materials, said at least one aperture being substantially the size of a hand, said top part further having a one-way barrier in said at least one aperture and comprising a closure flap molded into said top part along one edge of said flap to hinge said flap for inward deflection with respect to said top part upon insertion of said medical-surgical materials therethrough, and outwardly otherwise, said closure flap covering at least a portion of, said aperture, a flat, plastic cover slidably mounted to said top part and above said at least one aperture to permit said cover to be moved selectively over said at least one aperture to close all, some or none of said at least one aperture and wherein:

said top part is further provided with a plurality of fenestrations along said edge hinging said closure flap to said top part to permit said flap to be selectively broken away for removal from said aperture.

12. A rigid container for holding and disposing of used medical sharps and other medical-surgical materials comprising:

a molded, plastic bottom part having an open top with a flange molded thereon;

a plastic top part having an open bottom with a flange for mating with said bottom part flange molded thereon, said top part flange having a plurality of fastener means molded therein to engage said bottom part flange and fasten said top part to said bottom part without tools to form said container, said top part further having at least one aperture therethrough to permit the insertion therethrough of medical-surgical materials, said at least one aperture being substantially the size of a hand, said top part further having a one-way barrier in said at least one aperture and comprising a closure flap molded into said top part along one edge of said flap to hinge said flap for inward deflection with respect to said top part upon insertion of said medical-surgical materials therethrough, and outwardly otherwise, said closure flap covering at least a portion of, said aperture, a flat, plastic cover slidably mounted to said top part and above said at least one aperture to permit said cover to be moved selectively over said at least one aperture to close all, some or none of said at least one aperture and wherein:

said cover is provided with a pair of raised handle-stops at the front and back edges and a plurality of nose parts along the side edges; and said top part is provided with a pair of sliding rails on said top part, and a retaining flange to slidably retain said cover in position between said rails on said top part, said rails each having a plurality of detents to mate and engage with said nose parts of said cover to permit the position of said cover to be adjusted with respect to said aperture.

13. The rigid container of claim 12, wherein:

said retaining flanges each having a notched, down-turned portion intermediate of the length thereof to permit said cover to be installed below said flanges.

14. The rigid container of claim 12, wherein:

said sliding rails are separately molded parts with fasteners to fasten said rails to said top part and said top part has a plurality of fastener openings to receive said rail fasteners to hold said rails in place.

15. A container for holding and disposing of used medical sharps and other medical-surgical materials including a top part removably attached to a bottom part, said top part comprising:

a least one aperture providing a materials receiving opening of a sufficient size to allow manual insertion of said materials into said container;

a cover movably mounted to said top part including means for holding it in a normally open position, said cover being selectively manually movable to a closed position, and means for holding said cover in said closed position, whereby said materials receiving opening may be selectively closed only by an intentional manual manipulation of said cover from said open position to said closed position prior to disposal of said container; and a stationary barrier provided in addition to said cover which is positioned in said aperture and extends only partially across said materials receiving opening in a first direction and entirely across said opening in a second direction to normally provide a barrier against inadvertent release of materials inserted into said container when said cover is in said normally open position.

16. A container as in claim 15, wherein:

said barrier comprises a flap which is molded into said top part along one edge thereof to hinge said flap for inward deflection said flap extending substantially entirely across said aperture in said second direction which is parallel to said edge and only partially across said aperture in said first direction which is perpendicular to said edge.

17. A container for holding and disposing of used medical sharps and other medical-surgical materials including a top part removably attached to a bottom part, said top part comprising:

a least one aperture providing a materials receiving opening of a sufficient size to allow manual insertion of said materials into said container;

a cover movably mounted to said top part including means for holding it in a normally open position, said cover being selectively manually movable to a closed position, and means for holding said cover in said closed position, whereby said materials receiving opening may be selectively closed only by an intentional manual manipulation of said cover from said open position to said closed position prior to disposal of said container; and a barrier provided in addition to said cover which is positioned in said aperture and extending at least partially across said materials receiving opening to normally provide a barrier against inadvertent release of materials inserted into said container when said cover is in said normally open position wherein:

said barrier comprises a flap which is molded into said top part along one edge thereof to hinge said flap for inward deflection and wherein:

a plurality of fenestrations are provided in said top part along said edge of said flap to facilitate said flap being manually removed from said top part.

* * * * *

REEXAMINATION CERTIFICATE (1633rd)
United States Patent [19]
Sandel et al.

[11] B1 4,842,138
[45] Certificate Issued Jan. 28, 1992

[54] RIGID DISPOSABLE CONTAINER FOR HOLDING AND DISPENSING OF USED MEDICAL SHARPS AND OTHER MEDICAL-SURGICAL MATERIALS

[75] Inventors: Dan Sandel, Tarzana; Mike Hoftman, Northridge, both of Calif.

[73] Assignee: Devon Industries, Inc., Chatsworth, Calif.

Reexamination Request:
No. 90/002,075, Jul. 2, 1990

Reexamination Certificate for:
Patent No.: 4,842,138
Issued: Jun. 27, 1989
Appl. No.: 169,172
Filed: Mar. 10, 1988

Related U.S. Application Data

[63] Continuation of Ser. No. 838,296, Mar. 10, 1986.

[51] Int. Cl.⁵ .............................................. B65D 83/10
[52] U.S. Cl. .................................. 206/370; 206/363; 206/366; 206/438; 220/908; 220/345; 220/346
[58] Field of Search ................. 206/45.34, 363, 364, 206/366, 370, 438, 439, 571, 602, 621, 519; 220/908, 306, 345, 346

[56] References Cited

U.S. PATENT DOCUMENTS

| | | | |
|---|---|---|---|
| D. 264,879 | 6/1982 | Baker | 24/31 |
| 4,121,755 | 10/1978 | Meseke et al. | 229/38 |
| 4,315,592 | 2/1982 | Smith | 206/370 |
| 4,410,086 | 10/1983 | Simpson | 206/360 |
| 4,722,472 | 2/1988 | Bruno | 206/370 |
| 4,869,366 | 9/1989 | Bruno | 206/370 |

OTHER PUBLICATIONS

AMSCO Syringe Collection Container and System (1984 Brochures).

*Primary Examiner*—David T. Fidei

[57] ABSTRACT

A rigid, disposable container for safety containing and disposing of medical-surgical materials, including needles, syringes, scalpels and dressings after use, comprises five, lightweight plastic pieces which snap together without tools to form a closed container having a one-way barrier at a larger opening for the insertion of used materials therethrough, which barrier can be removed if desired, and additional apertures having sharps-removing features molded therein to permit the simultaneous removal of sharps from associated devices and their disposal therethrough. A flush, lockable, sliding cover is provided on the container to close the disposal openings against passage of macroscopic material either partially during use or completely before disposal.

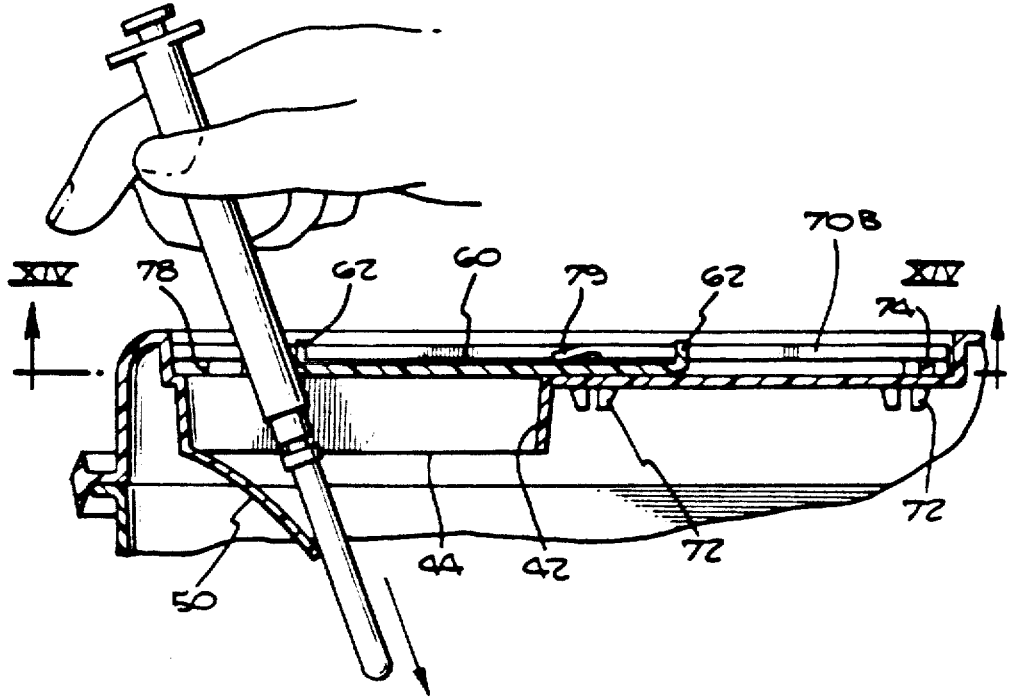

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 2, 4-9, 11-14 and 17 is confirmed.

Claims 1, 3, 10, 15 and 16 are cancelled.

New claim 18 is added and determined to be patentable.

*18. A container for holding and disposing of used medical sharps and other medical-surgical materials including a top part removably attached to a bottom part, said top part comprising:*

*an upper surface having a recessed portion;*

*at least one aperture within said recessed portion providing a materials receiving opening of a sufficient size to allow manual insertion of said materials into said container;*

*a cover movably mounted to said top part to close within said recessed portion and including means for holding it in a normally open position, said cover being selectively manually movable to a closed position within said recessed portion, and means for holding said cover in said closed position, whereby said materials receiving opening may be selectively closed only by an intentional manual manipulation of said cover from said open position to said closed position prior to disposal of said container; and*

*a single stationary barrier provided in addition to said cover which is positioned in said aperture and extends only partially across said materials receiving opening in a first direction and entirely across said opening in a second direction to normally provide a barrier against inadvertent release of materials inserted into said container when said cover is in said normally open position.*

* * * * *